(12) United States Patent　　(10) Patent No.: US 8,079,979 B2
Moorehead　　(45) Date of Patent: Dec. 20, 2011

(54) TRAPPING OF INTRAVENOUS NEEDLE ASSOCIATED WITH A LONG CATHETER, AND RELATED METHODS

(75) Inventor: H. Robert Moorehead, Salt Lake City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/254,328

(22) Filed: Sep. 25, 2002

(65) Prior Publication Data

US 2003/0032922 A1　Feb. 13, 2003

Related U.S. Application Data

(62) Division of application No. 09/465,431, filed on Dec. 21, 1999, now abandoned.

(51) Int. Cl.
*A61M 5/00* (2006.01)
*A61M 5/32* (2006.01)

(52) U.S. Cl. .................. 604/110; 604/198; 604/192

(58) Field of Classification Search .................. 604/110, 604/162, 171, 192, 198
See application file for complete search history.

(56) References Cited

U.S. PATENT DOCUMENTS

| | | | | |
|---|---|---|---|---|
| 3,515,137 A | | 6/1970 | Santomieri | 128/214.4 |
| 3,537,451 A | | 11/1970 | Beck et al. | 128/214.4 |
| 3,592,192 A | | 7/1971 | Harautuneian | 128/214.4 |
| 4,052,989 A | | 10/1977 | Kline | 128/349 |
| 4,388,074 A | | 6/1983 | Seberg et al. | 604/165 |
| 5,074,846 A | | 12/1991 | Clegg et al. | 604/164 |
| 5,137,515 A | * | 8/1992 | Hogan | 604/110 |
| 5,304,136 A | * | 4/1994 | Erskine et al. | 604/110 |
| 5,409,461 A | | 4/1995 | Steinman | 604/110 |
| 5,630,802 A | | 5/1997 | Moellmann et al. | 604/164 |
| 5,665,105 A | | 9/1997 | Furnish et al. | 606/205 |
| 5,823,997 A | * | 10/1998 | Thorne | 604/110 |

\* cited by examiner

*Primary Examiner* — Nicholas Lucchesi
*Assistant Examiner* — Victoria P Campbell
(74) *Attorney, Agent, or Firm* — Fay Kaplun & Marcin, LLP

(57) ABSTRACT

Apparatus and methodology are disclosed for entrapping a used intravenous needle in a needle trap and removing the needle and the trap from a catheter tube so as to avoid risk of injury to both the patient and the medical attendant.

19 Claims, 7 Drawing Sheets

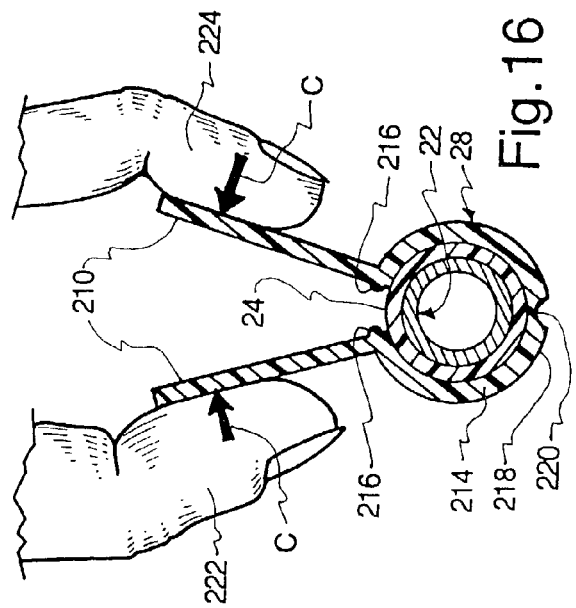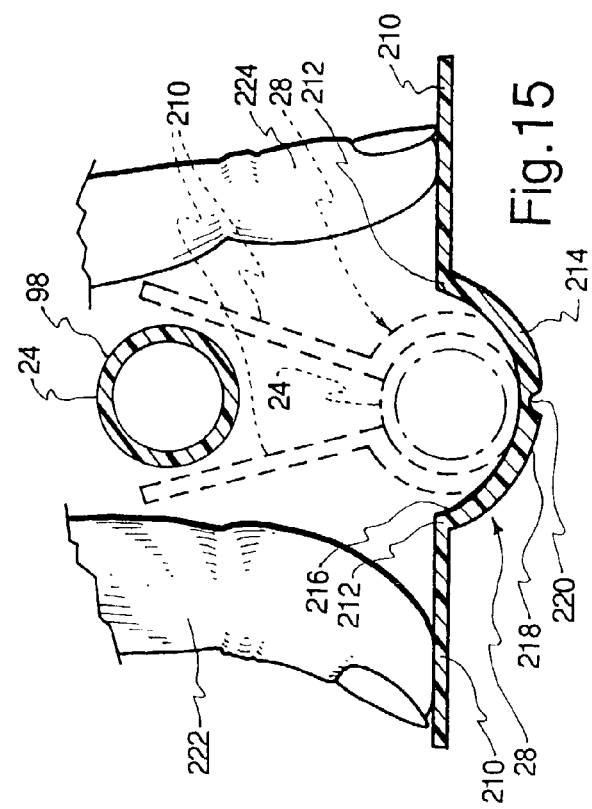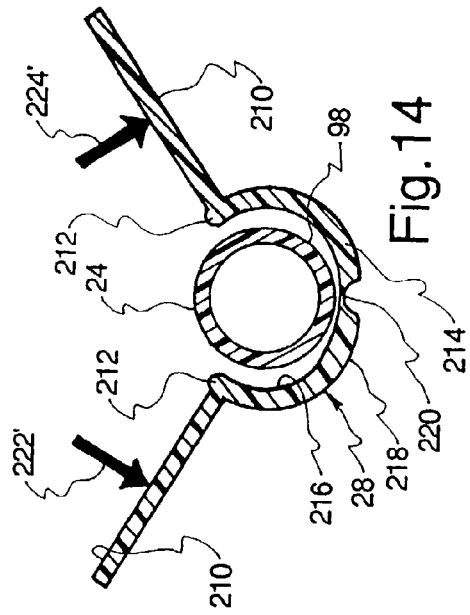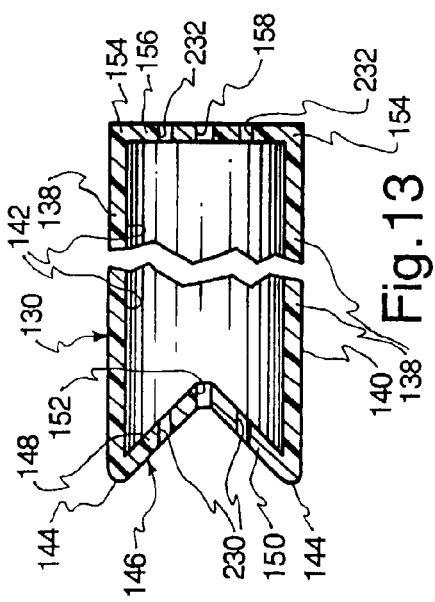

US 8,079,979 B2

TRAPPING OF INTRAVENOUS NEEDLE ASSOCIATED WITH A LONG CATHETER, AND RELATED METHODS

This application is a divisional of my U.S. patent application Ser. No. 09/465,431, filed Dec. 21, 1999, now abandoned.

FIELD OF THE INVENTION

The present invention relates generally to long intravenous catheter assemblies, such as central venous and peripheral catheter assemblies, and, more particularly to apparatus and methodology for fail-safe trapping of a used needle initially comprising part of a catheter assembly comprising a catheter tube and removal of the trap and the needle therein from the catheter tube. The invention is also useful with shorter catheter assemblies.

BACKGROUND

Disposal of used intravenous needles initially forming a part of a catheter assembly in a fail-safe way, so that inadvertent pricking of a medical aid provider or a patient is prohibited, has long been a problem in the medical field.

The present invention addresses this problem.

OBJECTS OF THE INVENTION

It is a primary object of the present invention to address the problem of disposing of intravenous needles, initially forming a part of a catheter assembly, in a fail-safe way.

It is another object to provide novel apparatus and methodology which address the problem mentioned immediately above.

These and other objects and features of the present invention will be apparent from the detailed description taken with reference to the accompanying drawings.

BRIEF DESCRIPTION OF THE DRAWINGS

FIG. 12 is an enlarged fragmentary cross-section of a needle trap, which initially forms a non-interference though contiguous fit within the catheter tube and, when the trap is pulled through a necked down region, an interference fit is formed to insure that the needle is fully seated within the trap before the trap with this needle therein is fully withdrawn from the catheter tube;

FIG. 13 is an enlarged fragmentary cross-section of a one-way gate of a needle trap which is pervious to liquid flow;

FIG. 14 is an enlarged cross-section of the insertion clamp of FIG. 1 with wings thereof partially spread;

FIG. 15 is an enlarged cross-section of the insertion clamp of FIG. 1 with wings thereof fully spread for removal of the catheter tube from the clamp; and FIG. 16 is an enlarged cross-section of an insertion clamp of FIG. 1 for inserting the catheter tube and needle into a vein and for advancing the catheter tube within the vein after retraction of the needle.

DETAILED DESCRIPTION OF THE ILLUSTRATED EMBODIMENTS

Reference is now made to the drawings, in detail, wherein like numerals are used to designate like parts throughout. It is to be appreciated that the presentation contained within this detailed description, in conjunction with the drawings, is not intended to provide a metes and bounds definition of the claimed invention, but rather is illustrative of some of the ways in which the broad invention may be specifically embodied, as currently contemplated by the inventor. The claims themselves are intended to define the metes and bounds of the present invention, which include combinations, sub-combinations, methods and sub-methods, all being within the scope of the present invention.

Figure 1:
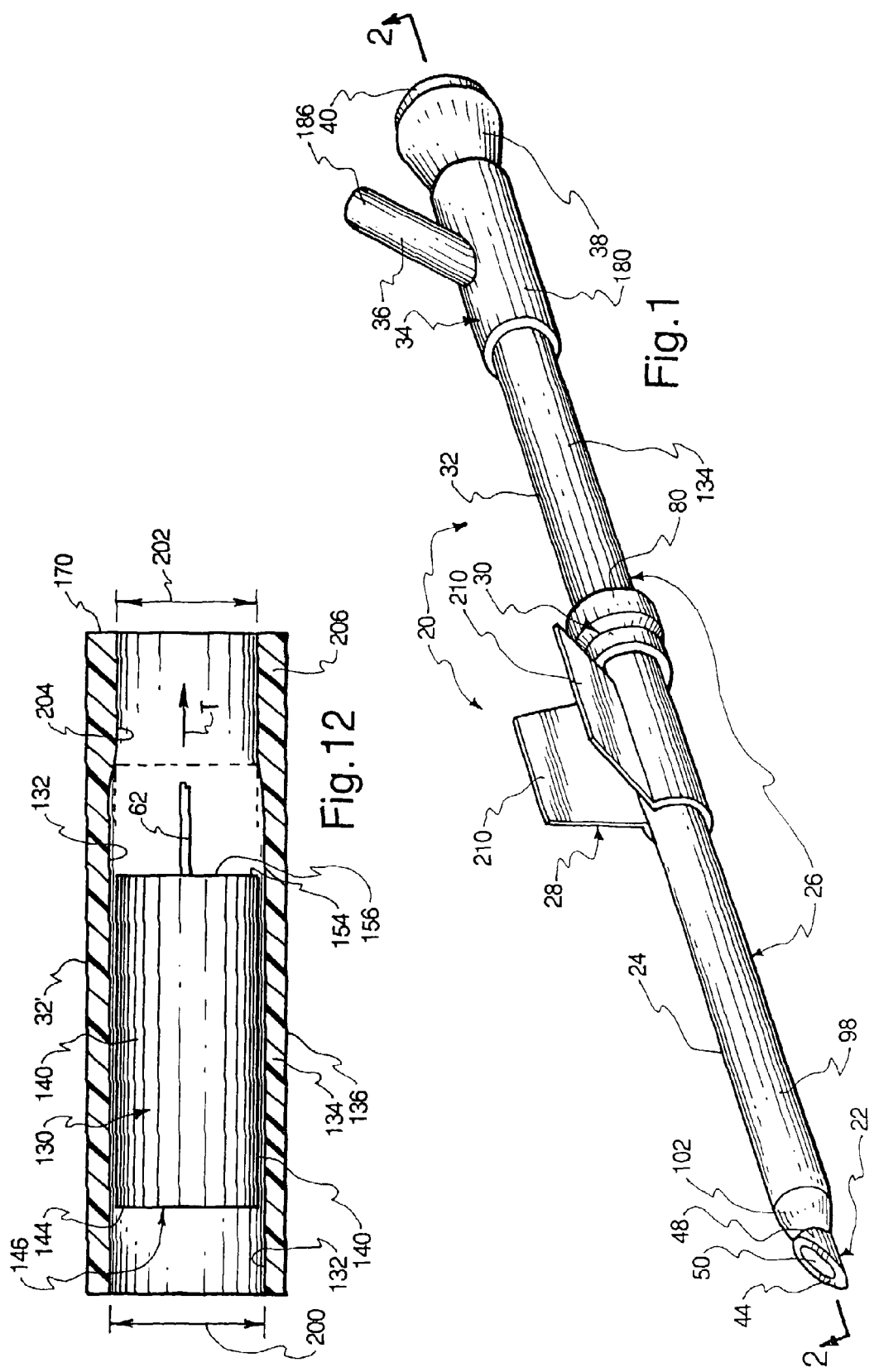
FIG. 1 is a perspective of one embodiment of the present invention.

FIG. 1 illustrates one configuration of many by which the present invention may be implemented. FIG. 1 illustrates an intravenous catheter assembly, generally designated 20. Assembly 20, as is illustrated in FIG. 1, comprises seriatim a needle, generally designated 22 for creating a venipuncture, a distal catheter tube segment 24 of a two-part catheter tube, generally designated 26, a clamp, generally designated 28, to aid in making the venipuncture and inserting the distal segment 24 of the catheter tube 26 into the vein as well as advancing it to a desired location after withdrawal of the needle 22. It is to be remembered that the catheter tube 26 and particularly the distal segment 24 thereof may be of any desired length so as to accommodate use thereof as a relatively short catheter or a much longer peripheral catheter or a central venous catheter. The catheter assembly 20 further comprises a slit-valve device, generally designated 30, located between the proximal end of the distal catheter tube segment 24 and the distal end of the proximal catheter tube segment 32 of the catheter tube 22. Connected at the proximal end of the catheter tube segment 32 is a Y-adapter, generally designated 34. The Y-adapter 34 comprises a side port 36 and an axially proximal hub 38 into which a plug 40 is illustrated as having been removably placed.

Figure 2:
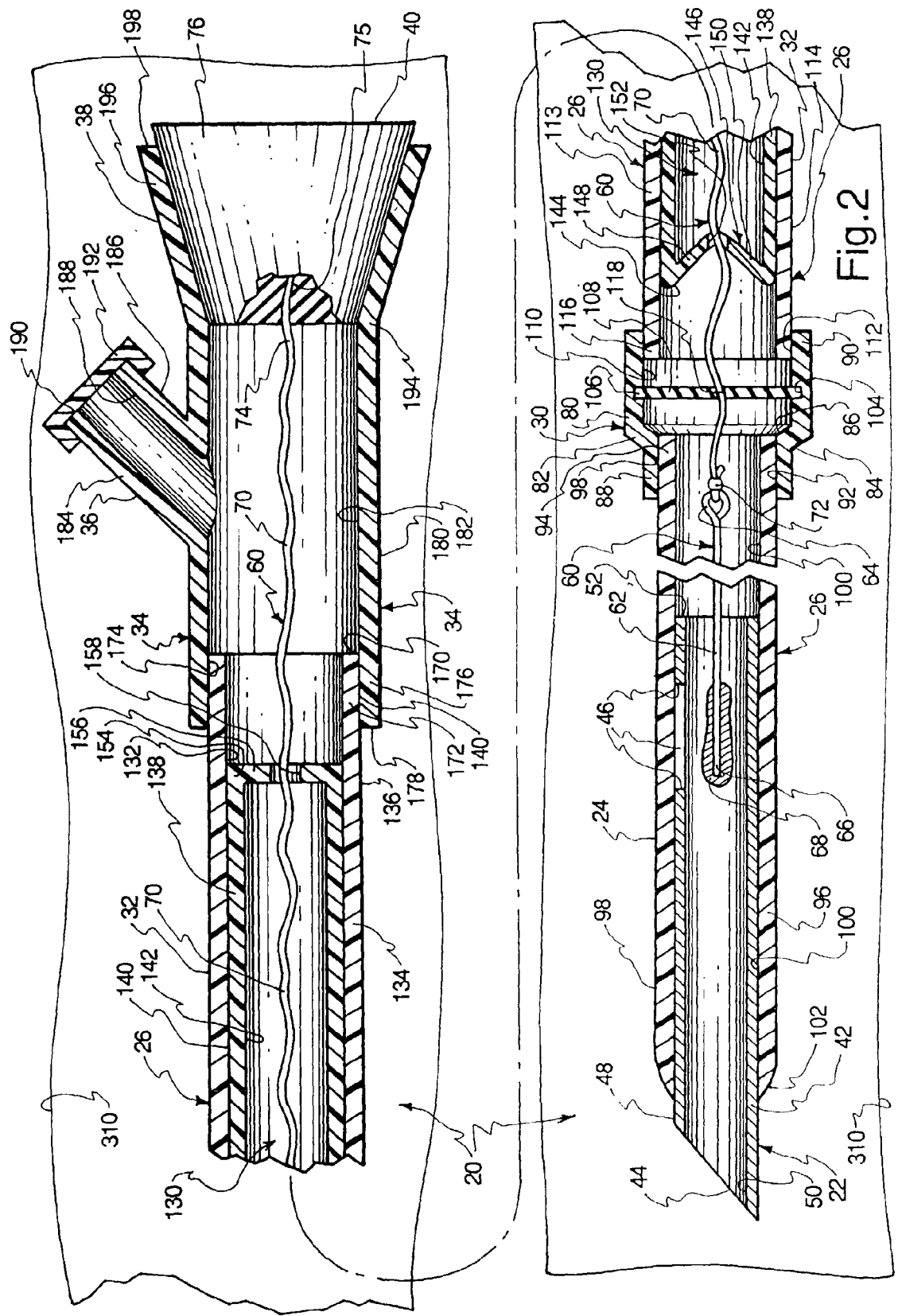
FIG. 2 is a cross-section taken along line 2-2 of FIG. 1, showing a control valve forward of a needle trap, with the catheter assembly being enclosed within a protective sheath.

Reference is now made to FIG. 2, which constitutes an axial or longitudinal cross-section taken along lines 2-2 of FIG. 1 and from which it can be seen that the various components of the assembly 20 may be formed for the most part of medical grade synthetic resinous material of suitable type. Some of the components of the assembly 20 comprise metal, silicone rubber and, in one embodiment, a fiber drawstring or tether component, as more fully hereinafter explained. As can be seen in FIG. 2, the needle 22 is illustrated as comprising a hollow metal tube, preferably of stainless steel, comprising a cylindrical wall 42 of uniform thickness, wall 42 having substantially uniform inside and outside diameters. Needle 22 is essentially of conventional manufacture, except for its specific configuration, including a relatively short length and other features of which accommodate its retraction as hereinafter more fully explained. Intravenous needle 22 comprises a beveled sharpened leading edge 44 to accommodate low trauma venipuncture. The wall 42 of the intravenous needle 22 comprises a window 46, illustrated as being rectangular but which may be of any suitable configuration so as to accommodate insertion, prior to assembly, of a welding tip for purposes yet to be explained. The outside surface 48 and the inside surface 50 of the needle wall 42 merge at beveled sharpened leading edge 44 and at blunt proximal end surface 52. End surface 52 is disposed, as illustrated, at a location distal of the proximal end of catheter tube segment 24.

It is, nevertheless, to be appreciated that the proximal end of the needle 22 could be at a location substantially common to the proximal end of the catheter tube segment 24.

If desired, a commercially available split sheath can be used in a conventional manner at the venipuncture site.

For needle removal purposes, the catheter assembly 20 is illustrated as comprising a composite tether or one-way needle retractor, generally designated 60. Tether 60 comprises, as illustrated, a slender rigid length of metal rod 62, preferably of shape-retaining stainless steel, which terminates in a proximal eyelet 64 and in a distal linear end 66, which is fused or connected by weldment 68 to the interior surface 50 of the needle 22. Access for creating the weldment 68 is provided, prior to assembly, by the window, slot or opening 46.

Composite tether 60 also comprises a yieldable or flexible segment 70, which may be a yieldable medical grade stainless steel metal wire, a synthetic resinous filament or a fibrous cord. Tether segment 70 is capable of transmitting tension to retract but incapable of transmitting compressive force to the rod 62, thereby limiting manual displacement of the needle 22 to retraction in a proximal direction, while prohibiting any displacement of the needle via this tether in a distal direction. In other words, if compression is applied to the tether segment 70, it collapses, buckles or relaxes without transmitting the compressive force to rod 62.

The yieldable tether segment 70 is illustrated as being connected to the rigid rod 62 at eyelet 64 using a suitable knot 72. Other forms of connection could be used. When rod 62 is formed metal, preferably the metal comprises a medical grade stainless steel.

The proximal end of the flexible segment 70 of the tether 60 is available at the proximal end of the assembly 20 for transmitting tension along the tether 60 to the intravenous needle 22 for retracting the same. The proximal end 74 of the tether segment 70 is to be made available in any suitable fashion at the proximal end of the assembly for withdrawal. One of several ways for doing this is illustrated in FIG. 2, i.e. the tether segment 70 is embedded at 75 in the elastomeric plug 40 and suitably secured therein so that the plug 40 may be manually grasped and a tensile force manually applied to the frusto-conical body 76 is transmitted along tether segment 70 and from thence to rod 62 and thereafter to the needle 22 through the weldment 68 to accommodate the withdrawal of the needle 22 in a proximal direction after the needle is used to make a venipuncture. Thus, plug 40 serves as a retraction handle.

The annular housing wall 80 of the valve device 30 is stepped at site 82 to form internal and external shoulders 84 and 86. Otherwise, the housing wall 80 is illustrated as being a wall of uniform thickness throughout which comprises a distal boss 88 and a larger proximal boss 90. Distal boss 88 has an interior annular surface 92, which is contiguous with and forms a lap joint against the proximal end 94 of the catheter tube segment 24. The catheter tube segment 24 is illustrated as being tubular so to comprise a wall 96 comprised of external and internal surfaces 98 and 100, each having a uniform diameter, and a tapered tip or beveled distal edge 102. The diameter of internal surface 100 is essentially the same as the diameter of the external surface 48 of the needle 22, the fit therebetween being somewhat loose to accommodate displacement of the needle 22 relative to the catheter tube segment 24 in a proximal direction for purposes and in a manner yet to be more fully explained.

The lap joint between surfaces 92 of the valve housing wall 80 and surface 98 of the catheter tube segment 24 at proximal end 94 comprises a bonded, welded or adhesively secured interface so that the wall 96 and the valve housing wall 80 are integrated and sealed. Note that the interiorly exposed portion of the valve housing wall 80 is transversely dimensioned so as to be materially greater than the diameter of catheter tube surface 100, again to facilitate a proximal displacement of the used needle 22. The housing wall 80 is diagramatically illustrated as comprising an internal annular groove 104 into which an annular edge 106 of diaphragm 108 is placed and held firmly in position, for example, by suitable bonding agent, welding or adhesive. If desired, the housing wall 80 may be otherwise constructed or configured so as to appropriately receive the diaphragm 108. The housing arrangement described in U.S. Pat. No. 5,201,722, owned by the assignee of the present invention may be utilized.

The proximal boss 90 of the valve housing wall 80 comprises an interior surface 110, the diameter of which is substantially the same as the outside diameter at surface 112 of the catheter tube segment 32. These contiguous surfaces form an interface which permanently unites the proximal end 90 of the valve housing 80 to the distal end 116 of the wall 113 of the catheter tube segment 32, using a suitable adhesive, welding or bonding agent. Thus, the tube 96, the housing 80 and the wall 113 collectively comprise a composite catheter tube for purposes of accommodating liquid infusion into and/or blood removal from a vein of a medical patient upon insertion of the distal end of the catheter tube segment 24 and the needle 22 from within the catheter tube, into the vein and removal of the needle 22 as hereinafter more fully explained.

The diaphragm 108 may be of any suitable material, preferably silicone rubber so that it is highly yieldable, biologically compatible with the human body and comprised of substantial memory so as to return to an unstressed normally-closed position after being stressed into an open position. The diaphragm 108 comprises a normally-closed central slit 118 through which the tether segment 70 passes when the assembly 20 is in its initial assembled condition. When the needle 22 is pulled in a proximal direction, the slit 118 dilates to accommodate passage of the needle 22 through the slit 118, following which the slit desirably returns to its normally closed condition requiring a pressure threshold between the pressure of the cardiovascular system and the pressure proximal of the diaphragm 108 in order to open again. In some cases, there is a possibility that slit 118 will not so return to its normally closed condition, in which case, a modest amount of leakage may take place across the diaphragm 108 after the needle 22 is retracted.

With continued reference to FIG. 2, a needle-trap, generally designated 130, is disposed internally within the catheter tube segment 32. Needle-traps are also sometimes known as needle safe devices, needle entrapment devices, needle shrouds, needle covers, needle guards, needle encapsulators and needle nests. The interior of catheter tube segment 32 is defined by an internal cylindrical surface 132 of wall 134. Wall 134 is illustrated as being of uniform thickness and comprising external cylindrical surface 136. The diameter of the interior surface 132 is greater than the diameter of the interior surface 100 of the catheter tube segment 24, thereby accommodating facile retraction of the needle 22 into the needle-trap 130.

The needle-trap 130 comprises a hollow cylindrical body defined by a cylindrical wall 138. Wall 138 comprises an external surface 140, the diameter of which is selected to provide a suitable loose fit with surface 132, to accommodate proximal withdrawal of the needle 22 into the trap and of the needle-trap 130 and the encapsulated needle 22 therein, out of the assembly 20 in a proximal direction, as hereinafter more fully explained. Wall 138 also comprises an internal cylindrical surface 142 defining a hollow interior needle-receiving chamber or capsule, the diameter of which is substantially greater than the diameter of surface 48 of needle 22 to accommodate entry of needle 22 into the needle-trap 130. Some resistance to relative displacement between segment 32 and trap 130 will exist at the interface between surfaces 132 and 140 so as to avoid inadvertent relative displacement of the trap 130 and to accommodate full entry of the used needle 22 into the trap.

Figure 8:
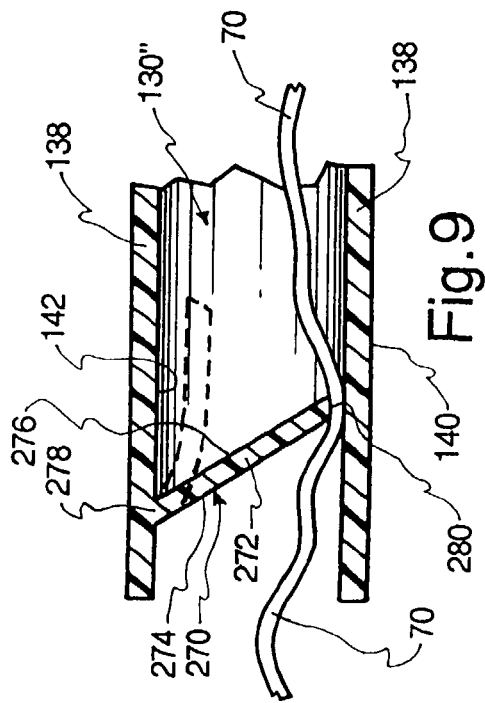
FIG. 8 is an end elevation of the bifurcated gate of the needle trap of FIG. 2.

Cylindrical wall 138 has an axial length substantially greater than the needle 22 to accommodate entry into and retention of the needle 22 within the hollow interior or compartment or receptacle at 142 of the needle-trap 130. The wall 138 terminates distally at an annular corner 144 and merges via corner 144 with a normally-closed proximally-directed diagonally-disposed one-way bifurcated needle entry gate, generally designated 146. The duck-bill distal entry gate, door or needle valve 146 is illustrated in FIG. 8, viewed in elevation from a distal location looking in a proximal direction with other parts removed. While other configurations could be used, gate 146 in FIG. 2 comprises a duck-bill valve comprised of upper and lower diagonally-directed proximally extending partable lips or flaps 148 and 150. Duck-bill lips 148 and 150 define an opening 152 therebetween, which is dilated radially and deflected proximally when the needle 22 engages and is displaced proximally against the distal sides of the lips 148 and 150, due to tension applied to the needle retraction tether 60, after which the memory of the material of which lips 148 and 150 is comprised returns the lips to their original unstressed position. The opening 152 accommodates passage therethrough of tether segment 70, in the initial assembled state as illustrated in FIG. 2.

The cylindrical or annular wall 138 of the needle-trap 130 terminates at proximal corner 154 and merges as one piece with a disc-shaped radial proximal wall 154, which centrally defines an aperture 158. The diameter of aperture 158 accommodates passage therethrough of tether segment 70, as illustrated in FIG. 2, but is substantially smaller than the diameter of needle surface 48 so that proximal displacement of the needle 22 beyond wall 156 is prohibited. It is to be appreciated that the degree of tightness between surfaces 140 and 132 should be of a magnitude which accommodates no relative displacement before and as the needle 22 is fully introduced into the needle-trap 130 but, thereafter accommodates displacement of the needle-trap 130 with the needle 22 therein from the catheter tube segment 32, responsive to sufficient tension applied to the composite tether 60. This tension is applied by manually gripping and retracting plug 40 from within the tapered hub 38, such force being applied in a proximal direction. The wall 134 of the catheter tube segment 32 terminates in a proximal blunt edge 170, which is in a plane substantially perpendicular to the longitudinal axis of the catheter tube segment 32 and forms a termination surface of the proximal portion 172 of the wall 134.

The proximal end 172 of the wall 134 forms a contiguous lap joint at the interface between surfaces 140 and 174 of the Y-Adapter at annular wall 176. The interface of surfaces 140 and 174 are glued, bonded or plastic welded together so that relative displacement is not possible and a liquid-tight seal is formed.

The annular wall 176 terminates in a distal blunt edge 178. The adapter blunt distal edge 178 is disposed essentially transverse to the longitudinal axis of the assembly. The wall 176 is illustrated as being of uniform thickness, except for side port 36, comprising an external cylindrical surface 180 and internal cylindrical surface 182. The wall 176 is interrupted by the side port 36, formed as one piece with wall 176 and comprising wall 184 shown as being of uniform thickness and comprising an exterior cylindrical surface 186 and an interior cylindrical surface 188. Wall 184 terminates in blunt transverse edge surface 190. The interior defined by surface 188 is closed by a cap or diaphragm 192 which prevents inadvertent fluid flow. Cap or diaphragm 192 may either be removed for attachment of a suitable medical fitting or may be constructed to accommodate penetration by a needle to infuse or remove a desired liquid. While not shown, tubular wall 184 may be equipped with threads for receiving either the cap 192 or a medical fitting, or both. It may also be equipped with a luer fitting configuration, as is common in the medical arts. The side port 36, among other things, accommodates flushing of the interior of the assembly 20 either before or after the needle removal or both. The provision of a side port at the proximal end of a catheter assembly is not essential to the present invention.

Annular wall 176 merges at corner 194 with the hub 38, which is illustrated as comprising a frusto-conical wall 196 shown as having a uniform thickness throughout and terminating in a proximal transverse edge surface 198. Wall 196 is sized and shaped so as to snugly receive plug 40 against inadvertent removal and so as to seal the plug 40 within the hub 38 while accommodating affirmative manual removal of the plug 40 to facilitate application of tension to the needle through force applied to tether 60, in the manner herein described. A replacement plug similar or identical to plug 40, without a connection to a tether, may be inserted into hub 38 once the needle-trap 130 with needle 22 therein have been removed from the assembly 20. The nature of a filling or adapter at the proximal end of a catheter tube is not an essential part of the present invention.

Reference is now made to FIG. 12, which illustrates a variation in the manner in which the proximal portion of the catheter tube segment 32 may be configured. More specifically, the proximal catheter tube segment 32 in FIG. 12 is designated by the numeral 32'. Catheter tube segment 32' is identical to catheter tube segment 30 except as hereinafter described. Identical or substantially identical parts in FIG. 12 when compared with those of FIG. 2 are so enumerated and no additional description thereof deemed necessary. The needle-trap 130 with the needle 22 disposed therein is illustrated as being positioned loosely within the hollow interior of the wall 134 of the proximal catheter tube segment 32'. While a space is shown between the interior cylindrical surface 132 of the wall 134 and the exterior surface 140 of the needle-trap 130, the two wall surfaces may be slightly contiguous so as to create a loose association allowing the needle-trap 130 to be readily displaced within the tube 134 upon the application of tension to the tether component 62.

Figure 6:
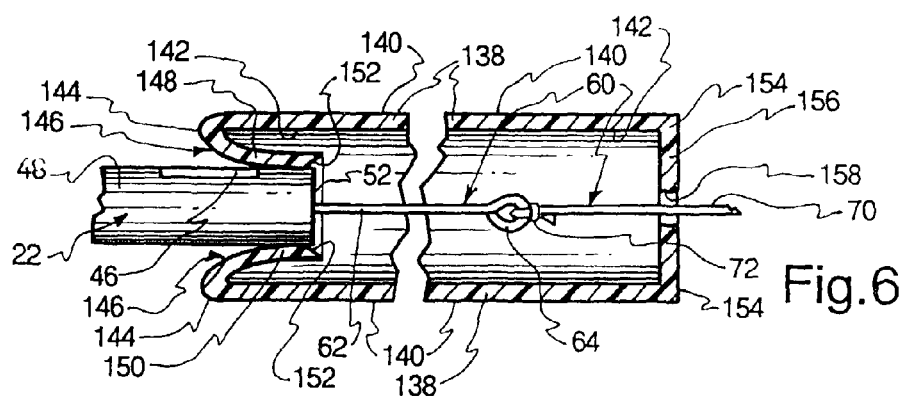
FIGS. 6 and 7 are cross-sections illustrating the manner in which the needle enters and becomes concealed within the needle trap of FIG. 2 through a one-way bifurcated gate.
Figure 7:
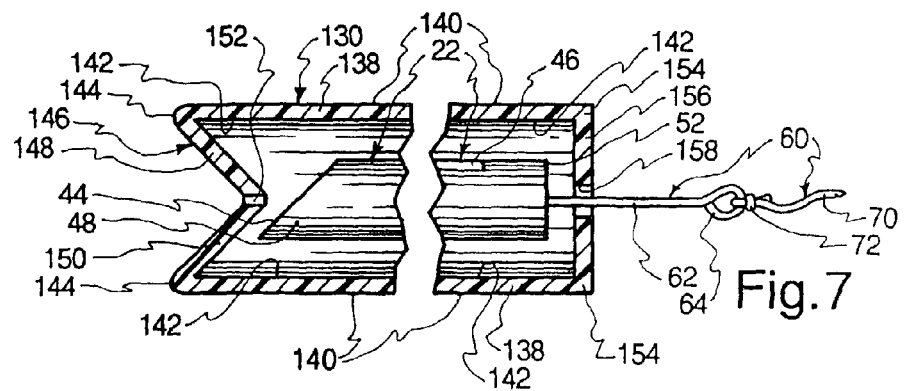

The diameter 200 defined by surface 132, at the distal end of the tube 134 is substantially greater than the diameter 202 defined by the annular surface 204 located at the proximal end 206 of the wall 134. This is because the thickness of the wall 134 is internally enlarged at proximal end 206 to form smaller diameter or constriction or necked down region 202. The diameter 202 is slightly less than the diameter of needle-trap surface 140 so that, as shown in dotted lines in FIG. 12, the proximal end of the needle-trap 140, at annular proximal corner 154 will engage the interior of the wall or necked down portion 206 during retraction to dilate the proximal wall surface 206 to a diameter greater than 202 and equal to the diameter of needle-trap surface 140 upon the application of sufficient tension "T" to tether portion 62. Thus, the needle-trap 130 will pass tightly and contiguously along the constriction at surface 204 with resistance from the catheter tube segment 32' and thence out of the catheter assembly 20 at the proximal portion thereof. The constriction at surface 204 therefore serves two purposes. First, the needle-trap 130 is prohibited from inadvertently being displaced from the catheter tube portion 32'. Second, when the trailing annular corner 154 of the needle-trap 130 engages the enlarged wall 206, greater tension "T" than would otherwise be the case is required to be applied to tether segment 62. This insures that the needle 22 fully enters and is immovably seated within the interior cavity of the needle-trap 30 with the distal gate 146 being returned to its closed position as illustrated in FIG. 2. The manner in which tension "T" applied to the tether 60 causes the needle 22 to enter the needle-trap 130 is best illustrated in FIG. 6, while the fully trapped or encapsulated needle 22 disposed within the needle trap 130 is best illustrated in FIG. 7.

In settings where fluid flow is desired, for flushing or any other reason, prior to removal of the needle 22 and the needle guard 30, additional apertures such as apertures 230 can be provided in lips 148 and 150 and apertures 232 can be provided in proximal end wall 156, so as to make the needle-trap sufficiently pervious. See FIG. 13. Thus, liquid can be infused through apertures 232 and 230 from a suitable source into the patient prior to removal of the needle 22 along with the needle-trap 130. Blood flashback, for example, can similarly take place prior to needle and needle-trap removal.

Reference is now made to FIGS. 14-16 for a greater description of the finger-held clamp or removable gripper 28, forming a part of the catheter assembly 20 of FIG. 1.

The clamp or inserter 28 is illustrated as being of one piece molded construction, formed of a suitable medical grade synthetic resinous material. The clamp or inserter 28 comprises a pair of generally rectangular jaws or wings 210, which extend in diverging relationship one to another when the clamp 28 substantially circumscribes the catheter tube distal segment 24, as best shown in FIGS. 1 and 16. The wings 210 are illustrated as being of uniform thickness, although other configurations could be used. Each wing merges at a longitudinally directed corner 212 with a central arcuately-shaped body of material 214, the axial length of which is illustrated as being essentially the same as the axial length of the wings 210. The axial body portion 214 comprises an internal concave surface 216 and an external convex surface 218. Surface 218 is centrally interrupted by an indentation comprising a living hinge 220, which accommodates pivoting of opposite halves of the clamp 28 in both directions to clamp for insertion (see FIG. 16) and to accommodate removal of the clamp from its initial surrounding location upon surface 98 of catheter tube segment 24 (see FIGS. 14 and 15). The memory of the material from which the clamp 28 is made tends to return the clamp to its initial non-stressed position illustrated in FIG. 1. In FIG. 15, fingers of the medical attendant, designated 222 and 224 are shown applying opening forces, while the application of force to open the clamp 28 is illustrated as force arrows 222' and 224' in FIG. 14.

Initially, with the clamp 28 near the distal end of the catheter tube segment 24, the fingers 222 and 224 are used to apply closing forces "C" upon the wings 210 which reduces the diameter of the surface 216 resulting in radial clamping pressure on the catheter tube segment 24 and upon the interior needle 22 initially disposed concentrically within the catheter tube segment 24. With pressure "C" being applied to the wings 210, as illustrated in FIG. 16, the medical attendant makes a venipuncture into the desired vein using the sharpened end 44 of the needle 22 as an instrument for entry. Once the needle 22 and the catheter tube segment 24 are suitably disposed within the selected vein, the needle 22 is retracted into the needle-trap 130 and the two are removed together from the proximal end of the assembly 20 responsive to the application of tension to the tether 60, as earlier explained.

Realizing that the assembly 20 may comprise a catheter tube segment 24 which has a very long length, for central venous and peripheral catheter use, for example, after removal of the needle 22 from within the catheter tube segment 24, the clamp 28, which initially is disposed near the distal end of the catheter tube segment 24, is retracted a short distance while in a loose state surrounding the exterior surface 98 of the catheter tube 24. Thereafter the needleless catheter tube is compressibly engaged by the clamp 28 in the manner explained above and illustrated in FIG. 16 and the catheter tube segment 24 is thereby advanced a greater distance into the vein. This clamp retraction and catheter tube and clamp advancement will continue in successive short increments until such time as the tip 102 of the catheter tube segment 24 is located at a desired site within the body of the patient being treated. At this time, forces 222' and 224' are applied to the wings as shown in FIG. 14, to accommodate a pivotal action of the wings 210 around living hinge 220 so that the enlarged diameter of the surface 216 accommodates removal of the clamp from the catheter tube segment 24, as illustrated in FIGS. 14 and 15. At this time, the exposed portion of catheter tube segment 24 and catheter tube segment 32 are taped to the arm to retain the tip 102 of the catheter tube at the desired internal location within the selected vein.

Figure 3:
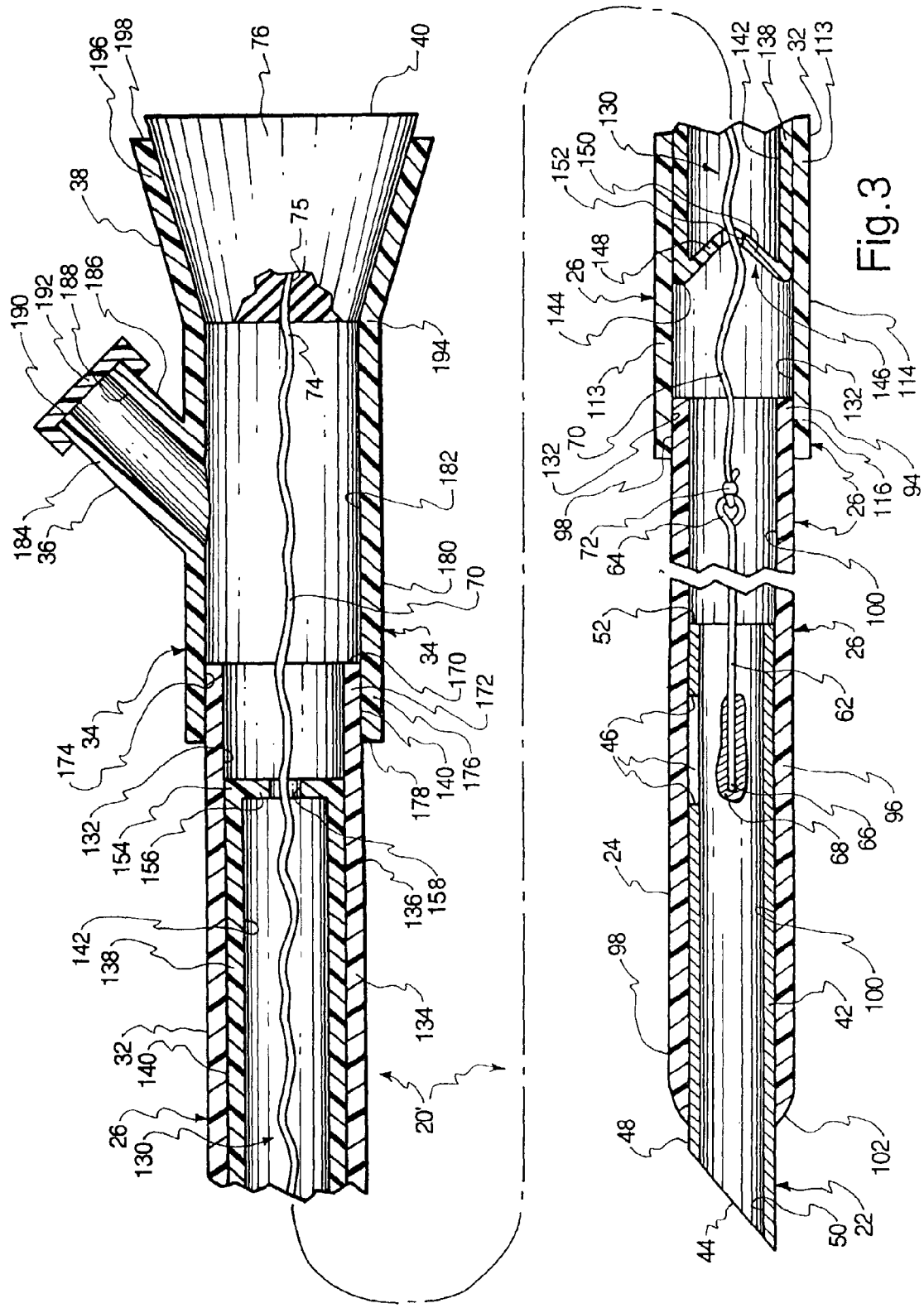
FIG. 3 is a cross-section, similar to FIG. 2, of another embodiment having no flow control valve per se.

It is to be understood that the present invention does not require, as an essential part thereof, a valve, including but not limited to the type of valve identified and described in reference to the numeral 30, interposed between two catheter tube segments. See FIG. 3, which illustrates in longitudinal cross-section, a catheter tube assembly 20'. Catheter assembly 20' is identical to catheter assembly 20 and the parts thereof are correspondingly enumerated, except valve 30 has been eliminated and in lieu thereof, a lap joint is provided between the proximal end portion 94 of the distal catheter tube segment 24 and the distal end portion 116 of the proximal catheter tube segment 32, i.e. at contiguous surfaces 98 and 132. The interface between surfaces 98 and 132 is sealed and integrated by use of a suitable adhesive or bonding agent or by plastic welding or in any other suitable fashion. Thus, the composite catheter tube of assembly 20' comprises only catheter tube segments 24 and 32, with no valve being included.

Figure 4:
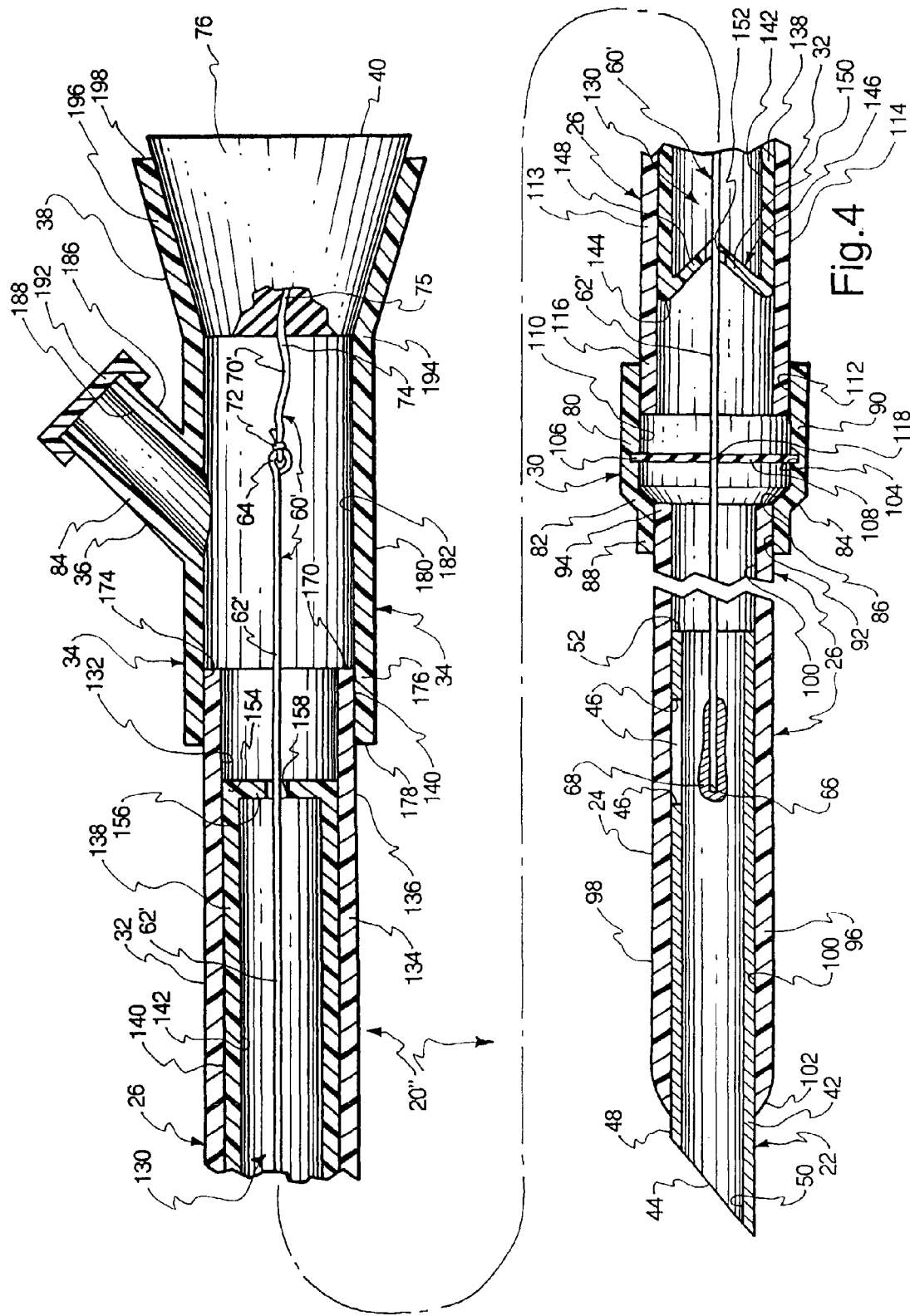
FIG. 4 is a cross-section, similar to FIG. 2, of a further embodiment having a flow control valve forward of a needle trap with a two-part needle-retracting tether where the distal part is longer than the proximal part of the needle-retracting tether, where the reverse is true of the embodiments of FIGS. 2 and 3.

It is to be understood that where a composite tether is utilized, the present invention is not restricted necessarily to a short rigid tether segment and a long flexible, non-compression transferring tether segment. Accordingly, in reference to FIG. 4 and catheter assembly 20", the rigid rod-like tether segment 62' is illustrated as being relatively long while the flexible tether segment 70' is illustrated as being relatively short. Together, the tether segments 62' and 70' comprise composite tether 60'. The other components of catheter assembly 20" are identical or substantially identical to the components of catheter assembly 20 as shown in FIG. 2. These components have been correspondingly enumerated in FIG. 4 to be identically to the enumeration contained in FIG. 2 and no further explanation thereof is deemed necessary.

Figure 5:
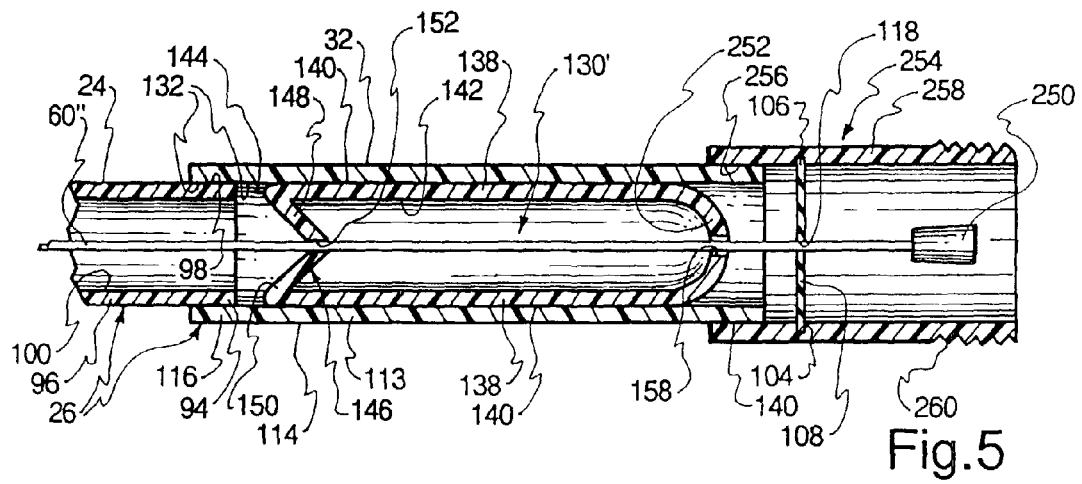
FIG. 5 is an enlarged fragmentary cross-section of another needle trap embodiment showing a control valve proximally disposed in respect to the needle trap.

The needle-retracting tether does not have to be composite in its construction in order to be within the scope of the present invention. As illustrated in FIG. 5, a single tether 60" may be provided which comprises a stainless steel wire welded at the distal end thereof to the needle 22, or a monofilament or fibrous strand glued, bonded or otherwise suitably secured to the needle 22 or, in some configurations, a stainless steel rod. A handle 250 is integrally provided at the proximal end of the tether 60", which may be manually grasped to accommodate displacement of the needle 22 in a proximal direction into a needle trap, generally designated 130'. Needle-trap 130' is identical in all respects to needle-trap 130, except the proximal wall 252 is illustrated as being rounded or bullet-shaped in its configuration as opposed to the square or blunt wall 156 of the needle-trap 130.

In addition, the embodiment of FIG. 5 illustrates that, if desired, a valve mechanism, generally designated 254 may be used at a location proximal of the needle-trap 130'. Valve 254 is illustrated as forming a lap joint, at surface 256, with surface 114 of proximal catheter tube segment 32, which interface is secured by bonding, adhesive, plastic welding or like so as to integrally unite catheter tube segment 32 and valve housing 258 of the valve 254 in sealed relationship. The valve 254 comprises previously described diaphragm 108 with central slit 118 therein held at the peripheral edge 106 in groove 104 in any suitable way including but not limited to use of adhesive, bonding agent or plastic welding. The tether 60', in the initial assembled condition, passes through the slit 118.

The valve housing wall 258 is illustrated as being provided with proximal threads 260 by which an infusion or other tube may be conventionally connected. In lieu of the threads 260, a male luer or a force-fit union may be provided.

In operation, the medical technician grasps the handle 250 and pulls in a proximal direction, causing the pulling or tensile force to be transmitted along tether 60" to the used intravenous needle 22. Proximal displacement of the needle continues, responsive to the tension applied to tether 60", until such time as the needle 22 is seated, encapsulated or fully contained within the needle-trap 130', in the manner explained above. Thereafter, continuing tension applied to tether 60" displaces the needle-trap 130', with the needle 22 therein, against and through the diaphragm 108, the slit 118 dilating to accommodate full removal of the encapsulated needle 22, the needle-trap 130' and the tether 60". The resilient nature of the diaphragm 108 will, thereafter, normally cause the slit to return to a normally closed state. In instance where the slit 118 does not fully close, the amount of liquid leakage across the slit 118 would be minimal. This leaking, if any, if initially relevant would become irrelevant once a suitable medical tubing is connected to the valve housing 258 at threads 260.

The one-way valve gate or entry door to a needle-trap, in accordance with the present invention need not necessarily be constructed in a duck-bill fashion as illustrated and described above. Any suitable one-way needle entry gate, door, flap or closure structure which accommodates full entry of the used needle 22 and prevent subsequent partial or total displacement of the used needle from the needle-trap in a distal direction is suitable.

Figure 9:
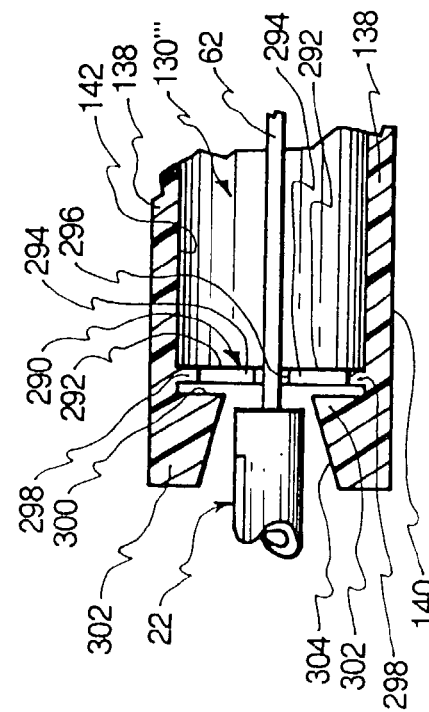
FIG. 9 is an enlarged fragmentary cross-section of a different single-flap one-way gate for a needle trap.

For example, the one-way needle entry gate, generally designated 270 in FIG. 9 may be used, so as to form an integral part of needle-trap 130". Needle-trap 130", except for entry gate 270, is the same as previously described needle-trap 130 and, therefore, no further description other than in respect to gate 270 is deemed necessary. Entry gate 270 comprises an oval-shaped planer wall 272, illustrated as having uniform thickness throughout, which defines an exterior surface 274 and an interior surface 276. The wall 270 is formed as one piece with the cylindrical body wall 138 of needle-trap 130". Thus a living hinge, at 278, is provided which accommodates pivoting of the wall 272 from the position illustrated to a deflected, proximally extended position, shown in dotted lines in FIG. 9, sufficiently out of the way to accommodate entry of the used needle 22 into the hollow interior at 142 of the needle-trap 130" upon application of suitable tension to the tether component 70. After the needle 22 is confined within the needle trap 130", the memory of the material from which the wall 272 is made returns the wall 272 to its unstressed condition illustrated in FIG. 9. Initially, in an unstressed condition, the wall 272 extends diagonally, as shown in FIG. 9, in a somewhat proximal direction from living hinge 278 to the zenith of an end edge surface 280. Edge 280 is spaced from the interior surface 142 at the zenith a distance sufficient to accommodate passage of the tether component 70 therethrough.

The periphery or perimeter of the wall 272 is unattached to the wall 130, except for the attachment at living hinge 278, thereby accommodating pivoting of the wall 272 from the solid line to the dotted line position illustrated in FIG. 9, to accommodate full entry of the used needle 22. The wall 272 is of a size and nature so that reverse pivoting in a distal direction is prohibited, preventing exiting of the entrapped used needle 22 in a distal direction. Thus, wall 272 functions as a one-way entry valve, door or gate for accommodating proximal displacement of the used needle 22 into the cavity or component defined by surface 142, while prohibiting reverse displacement of the used needle 22 once the needle 22 is entirely within the encapsulating chamber defined by wall surface 142.

Figure 11:
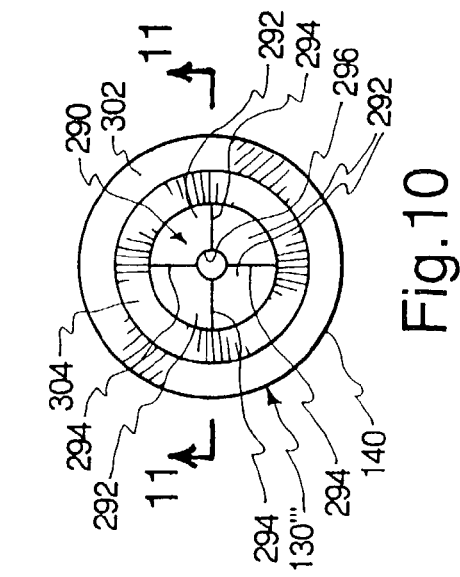
FIG. 11 is a fragmentary cross-section taken along lines 11-11 of FIG. 10.
Figure 10:
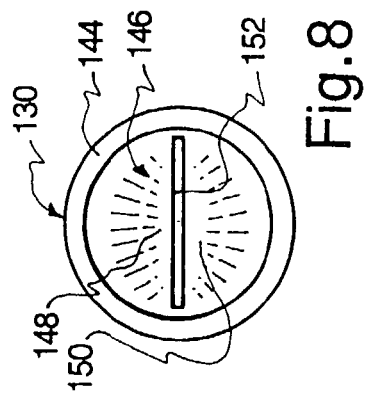
FIG. 10 is an end elevation of a multiple flap one-way gate for a needle trap.

Reference is now made to the needle-trap entry gate embodiment illustrated in FIGS. 10 and 11, which is generally designated 290. Needle entry gate 290 forms an integral part of a needle-trap generally designated 132'''. Except for entry gate 290, needle-trap 130''' is constructed identical to needle-trap 130 and has been correspondingly enumerated in FIGS. 10 and 11, thereby obviating any need for a further description of these needle-trap components.

The entry gate 290 comprises a plurality of radially directed flaps 292, which are divided into quadrants, with a slit 294 disposed between each two adjacent quadrant flaps 292. Of course, any number of flaps may be used as determined by those of skill in the art. Collectively, the quadrant flaps 292 define a central aperture 296 the diameter of which is somewhat greater than the diameter of the tether component 62, thereby allowing the tether component 62 to freely pass through the aperture 296, as illustrated in FIG. 1. Each quadrant flap 292 comprises a living hinge 298 where the quadrant flap joins as one piece the needle-trap wall 138. The four living hinges extend essentially 90 degrees respectively along the periphery of the flaps when considered collectively and accommodate proximal deflection of each flap when engaged by the used needle 22 thereby facilitating full entry of the used needle 22 being displaced proximally into the compartment defined by needle-trap wall surface 142.

Distal rotation of the quadrant flaps 292 about their respective living hinges 298 is prohibited by an annular stop surface 300'. Stop surface 300' is juxtaposed the distal surfaces of the quadrant flaps 292. The annular surface 300 comprises part of a distal abutment wall 302 formed as one-piece with wall 138, which is distal of the quadrant flaps 292 but sized so as to provide a tapered aperture 304, the minimum diameter of which is greater than the diameter of the needle 22 thereby providing a centering entry site of sufficient size to accommodate introduction of the used needle 22 into the needle-trap chamber defined by wall surface 142.

From the foregoing, it is understood that apparatus and methodology are provided for encapsulating a used needle without allowing exposure of the sharpened distal tip of the needle to human contact (either by the patient or the medical attendant). This involves creating a venipuncture using the sharp distal tip of the needle followed by insertion into the selected vein of the distal end of the needle as well as the distal end of the catheter tube surrounding the needle. Thereafter, a slender tether or needle-pulling device is used to transmit tension to the needle causing the needle to retract proximally along the interior of the catheter tube so that the sharpened point is concealed within the hollow interior of the catheter tube. The used needle continues to be shielded or concealed as the needle is pulled a greater distance along the interior of the catheter tube through a one-way gate into a hollow interior of the needle-trap capsule. The capsule, with the needle contained therein is thence retracted collectively from the catheter assembly through the proximal end thereof and discarded. Thus, at no time after venipuncture, is the sharpened end of the needle exposed for human contact.

It is to be understood that after manufacture, during storage and prior to use, a conventional cover sheath may be placed over the exposed sharpened end of the needle as well as the distal end of the catheter tube, in a manner well understood and known in the industry. Furthermore, the entire catheter assembly may be encapsulated within a flexible protective sheath 310 (FIG. 2), normally transparent film, after manufacture and prior to use to prevent or alleviate certain risks of contamination, as is also conventional in the medical field.

While certain presently preferred materials have been disclosed, any suitable material may be used for any component.

The invention may be embodied in other specific forms without departing from the spirit or essential characteristics thereof. The present embodiments are therefore to be considered in all respects as illustrative and not restrictive, the scope of the invention being dictated by the appended claims rather than by the foregoing description, and all changes, which come within the meaning and range of equivalency of the claims are therefor intended to be embraced therein.

What is claimed and desired to be secured by Letters Patent is:

1. A needle trap for fail-safe storage of a used withdrawn intravenous needle comprising a body defining a hollow needle-receiving chamber therein to accommodate a proximal withdrawal of the needle, the trap further comprising a distal end and a proximal end, the distal end comprising a one-way valve gate to the chamber through which the needle is displaced and which thereafter prevents distal displacement of the needle from the trap, the proximal end of the trap comprising an abutment preventing proximal displacement of the needle from the trap, wherein, when the one-way valve gate is in an unstressed state, the one-way valve gate defines a rectangular slot opening when viewed from a distal location in a proximal direction and at least one additional aperture extending through the one-way valve gate and offset from the rectangular slot opening.

2. A needle trap according to claim 1 wherein the one way valve gate comprises bifurcated lips.

3. A needle trap according to claim 2 wherein the lips comprise part of a duckbill valve gate.

4. A needle trap according to claim 1 wherein the valve gate comprises at least one flap hinged at a predetermined site to accommodate proximal deflection when forcibly contacted by the needle.

5. A needle trap according to claim 4 wherein the hinge is a living hinge.

6. A needle trap according to claim 4 wherein the at least one flap is selected from the group consisting of one, two and more than two flaps.

7. A needle trap according to claim 1 wherein distal displacement of the valve gate from an at rest position is prevented by at least one of: a stop structure and a diagonal proximally-directed gate construction.

8. A needle trap according to claim 1 wherein the valve gate and the abutment define passageways through which a pull tether extends.

9. The needle trap according to claim 8, further comprising at least one additional proximal aperture extending through a proximal end of the needle trap, the at least one additional proximal aperture being offset from a tether aperture configured to permit insertion of the tether therethrough.

10. A needle trap for storage of a used intravenous needle comprising:
a needle-receiving chamber including a one-way valve gate to the chamber at a distal end thereof through which the needle is withdrawn after performing a target procedure and which then prevents the needle from exiting the needle trap, the one-way valve gate, when in an unstressed state, defining a slot opening and a first aperture extending through the one-way valve gate offset from the slot opening, a proximal end of the needle receiving chamber comprising an abutment preventing proximal displacement of the needle from the trap.

11. The needle trap according to claim 10, wherein a proximal end of the needle-receiving chamber comprises an abutment preventing proximal displacement of the needle from the trap.

12. The needle trap according to claim 10, wherein the slot opening is substantially rectangular.

13. The needle trap according to claim 10, wherein the one-way valve gate includes opposed lips biased toward the unstressed state, a separation between the lips forming the slot opening.

14. The needle trap according to claim 10, further comprising a pull tether extending through the trap via passageways through the valve gate and the abutment.

15. The needle trap according to claim 14, further comprising a proximal aperture extending through a proximal end of the needle trap offset from the passageway through which the tether extends.

16. The needle trap according to claim 10, wherein the valve gate comprises a flap hinged to accommodate proximal deflection when forcibly contacted by the needle.

17. The needle trap according to claim 10, wherein distal displacement of the valve gate from a rest position is prevented by at least one of a stop structure and a diagonal proximally-directed gate construction.

18. A needle trap comprising a body defining a hollow needle-receiving chamber therein, a distal end of the body comprising opposed one-way valve flaps to the chamber movable proximally to a needle receiving position by proximally directed force applied as a needle is withdrawn proximally into the needle-receiving chamber, the flaps being biased to return to a locking position after a distal end of the needle has passed proximally therepast wherein, in the locking position, a slot opening remaining between the flaps is sized to prevent a needle received in the needle-receiving chamber from passing therethrough out of the needle-receiving chamber, the proximal end of the trap comprising an abutment preventing proximal displacement of the needle from the trap, the body further comprising an aperture extending through the opposed one-way valve flaps offset from the slot opening.

19. The needle trap according to claim 18, wherein the opposed one-way valve flaps are coupled to a wall of the needle-receiving chamber via a living hinge and extend proximally at an angle relative to the wall into the needle-receiving chamber.

* * * * *